US008377141B2

United States Patent
McMinn

(10) Patent No.: US 8,377,141 B2
(45) Date of Patent: Feb. 19, 2013

(54) KNEE PROSTHESIS

(76) Inventor: Derek James Wallace McMinn, West Midlands (GB)

( * ) Notice: Subject to any disclaimer, the term of this patent is extended or adjusted under 35 U.S.C. 154(b) by 1733 days.

(21) Appl. No.: 11/351,607

(22) Filed: Feb. 10, 2006

(65) Prior Publication Data

US 2006/0265078 A1 Nov. 23, 2006

(30) Foreign Application Priority Data

May 19, 2005 (GB) .................................. 0510194.4

(51) Int. Cl.
*A61F 2/38* (2006.01)
*A61B 17/15* (2006.01)

(52) U.S. Cl. ...................... 623/20.35; 606/88

(58) Field of Classification Search .............. 623/20.14, 623/20.19, 20.21–20.31, 20.35–20.36; 606/86 R, 606/87, 88
See application file for complete search history.

(56) References Cited

U.S. PATENT DOCUMENTS

| 5,116,375 | A | 5/1992 | Hofmann | |
| 5,387,240 | A | 2/1995 | Pottenger et al. | 623/20 |
| 5,658,342 | A | 8/1997 | Draganich et al. | 623/20 |
| 5,702,460 | A * | 12/1997 | Carls et al. | 606/79 |
| 5,824,100 | A | 10/1998 | Kester et al. | |
| 6,168,629 | B1 | 1/2001 | Timoteo | |
| 6,364,911 | B1 * | 4/2002 | Schmotzer et al. | 623/20.31 |
| 6,413,279 | B1 * | 7/2002 | Metzger et al. | 623/20.29 |
| 6,503,254 | B2 * | 1/2003 | Masini | 606/86 R |

FOREIGN PATENT DOCUMENTS

| EP | 0773756 B1 | 10/2002 |
| EP | WO2004069104 A1 | 8/2004 |
| GB | 2387546 B | 12/2004 |
| WO | WO2004158108 A1 | 7/2004 |

* cited by examiner

*Primary Examiner* — Thomas J Sweet
*Assistant Examiner* — Megan Wolf
(74) *Attorney, Agent, or Firm* — Foley & Lardner LLP

(57) ABSTRACT

A femoral component of a knee prosthesis comprises a femoral flange from an inner end of which extend lateral and medial condylar parts which are interconnected by a box-like bridging part at an intercondylar groove. The interior surface of the femoral component has six discrete flat sections, with the sixth flat section which extends to a free end of the femoral component being angled relative to a plane normal to the third flat section and to the length of the intercondylar groove. Also disclosed is a trial femoral component and a method of use thereof to prepare a femur for the fitting of the femoral component of the prosthesis.

16 Claims, 5 Drawing Sheets

KNEE PROSTHESIS

CROSS REFERENCE TO RELATED APPLICATION

This application relates to and claims priority to corresponding Great Britain Patent Application No. 0510194.4, which was filed on May 19, 2005, and which is incorporated by reference herein.

BACKGROUND OF THE INVENTION

1. Field of the Invention

This invention relates to a knee prosthesis for fitting to a patient as a replacement knee joint.

2. Related Art

Modern total knee replacement involves the resurfacing of the femoral condyles with a metallic component, roughly approximating to the shape of the anatomical femoral condyles, and resurfacing the tibial plateau with a polyethylene component having a metallic base plate.

One problem with such total knee replacement relates to the matching of the interior surface of the femoral component of the implant with the resected distal anterior surfaces of the femur. FIG. 1 shows a femoral bone, and from this it can be seen that the lateral femoral condyle (LFC) is longer than the medial femoral condyle (MFC) and that the condyles blend with the shaft of the femur in a different way on each side. A line connecting the points AM-AL makes an angle to the line connecting the points PM-PL. This presents the surgeon with a problem. Traditionally the distal end of the femur is cut with a cutting block and oscillating saw and generally five flat cuts are made. It used to be normal practice to insert the femoral component parallel to the line PM-PL and it can be seen that when a line parallel to this is made anteriorly, then AM and AL do not match the anterior cut. It has been discovered over the years that by externally rotating the cuts, and thus the femoral component, along the line EM-EL, the patellar track tends to be placed more in line with the normal patellar track P-P, and hence there is a feeling that better patellar tracking is achieved with an externally rotated femoral component. This provides a problem with the anterior cut because since the anterior cut in conventional Total Knee Replacements has to be parallel to the posterior cut EM-EL, then there is really no way of accurately matching up the bony landmarks AM-AL to the externally rotated anterior cut. The surgeon has two options. Firstly he can clear the bone at point AL and leave a gap medially between AM and the undersurface of the medial flare of the prosthesis. Alternatively, he can bring the anterior cut down to AM and make a notch into the lateral femur at point AL. This has the serious undesirable feature that digging a notch in the bone weakens the femur, causes a stress riser and, particularly in elderly ladies with brittle bones, risks a supra-condylar fracture of the femur.

SUMMARY OF THE INVENTION

The present invention seeks to obviate or at least minimize this problem.

According to a first aspect of the invention there is provided a femoral component of a knee prosthesis comprising a femoral flange from which extend lateral and medial condyles with an intercondylar groove there between, the condyles defining respective co-planar interior flat surfaces aligned at opposite sides of said intercondylar groove to engage, in use, with respective flat lowermost surfaces of a resected femur, a part of the femoral flange extending to a free end of the femoral component having a flat internal surface angled relative to a plane which is normal to said flat surfaces and to the length of said intercondylar groove.

Preferably the part of the femoral flange is angled by a value in the range of approximately 3° to approximately 20°, and more preferably by 10°, relative to said plane. Desirably an internal surface of the femoral flange extending away from said flat surfaces at opposite sides of the intercondylar groove is formed as three flat sections at respective different angles relative to said plane. Conveniently the interior of the femoral component is formed as six discrete flat sections.

The invention also relates to a trial femoral prosthesis component.

BRIEF DESCRIPTION OF THE DRAWINGS

The invention will now be described, by way of example, with reference to the accompanying drawings, in which.

DETAILED DESCRIPTION OF THE INVENTION

Figure 2:
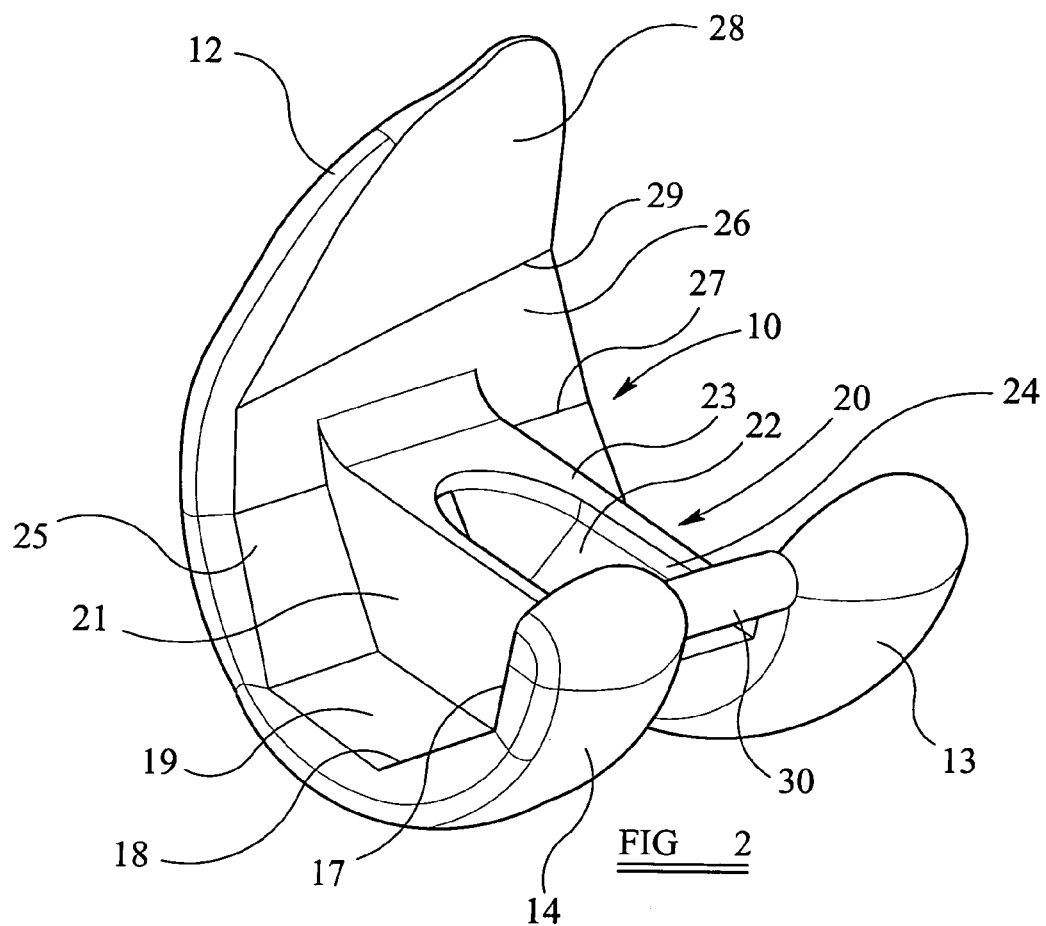
FIG. 2 is a perspective view of a femoral component of a replacement knee prosthesis, the femoral component being according to the invention.

The invention relates to a femoral component of a knee prosthesis, the femoral component being shown alone in FIG. 2.

Figure 3:
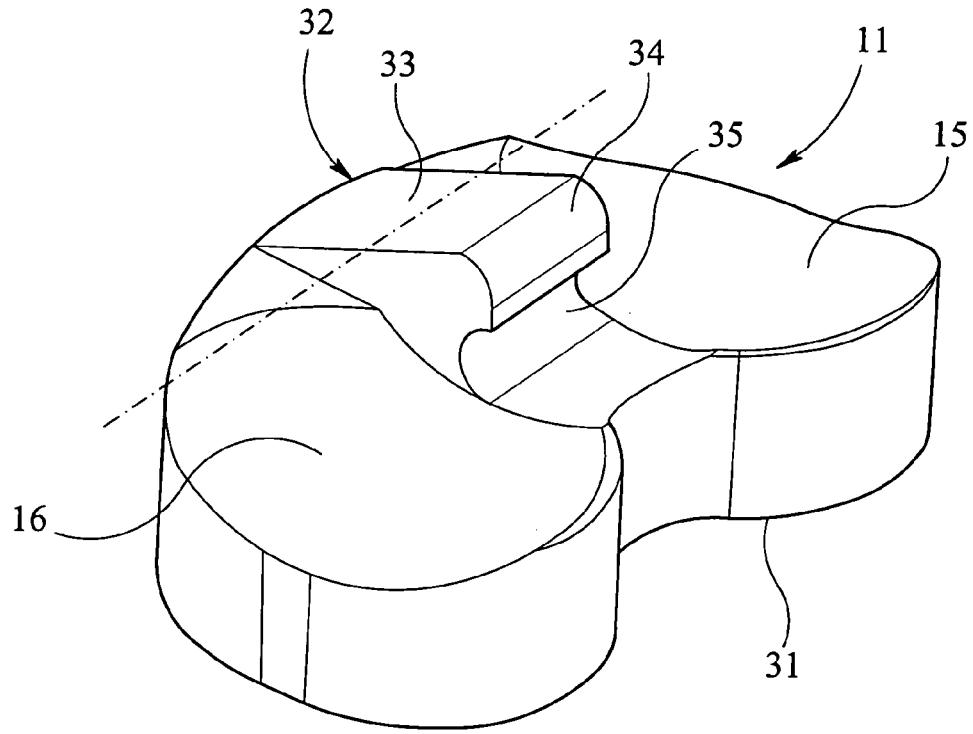
FIG. 3 is a perspective view of a bearing component of the replacement knee prosthesis.

As is well known, a knee prosthesis generally comprises a femoral component, a tibial component, and a meniscal or bearing component. Generally the femoral and tibial components are of metal with the bearing component being of plastics material such as polyethylene and fitting between the femoral and tibial components. In the accompanying drawings the tibial component is not shown, but it is to be understood that this would generally be of conventional form, such as in U.S. Pat. Nos. 5,387,240 and 5,658,342 having a flat upper surface in use, on which the flat lower surface of the bearing component engages, and a depending lower fixing stem. In FIGS. 2 and 3, the femoral component is indicated by the numeral 10 and the bearing component is indicated by the numeral 11.

The knee replacement device shown in the drawings is of bicondylar form, with the femoral component 10 being a bicompartmental component. This is generally of known form defining a pair of spaced 'rounded' surfaces corresponding substantially to the condyles of the normal femur, i.e. the medial and lateral condyles thereof, the component 10 being a single one-piece construction.

The femoral component 10 is generally C-shaped, as shown in FIG. 2, comprising a femoral flange 12 from the inner end of which extend spaced parallel lateral and medial condylar parts 13, 14 respectively, the respective undersurfaces of these condylar parts being part-spherical to mate, in use, in the normal way with the corresponding part-spherical surfaces 15, 16 of bearing component 11 shown in FIG. 3.

As can be seen from FIG. 2, the interior surface of each of the condylar parts 13, 14 is formed in three flat sections, a first flat section 17 of which is generally vertically upright, in use, when there is 0° of flexion of a knee to which the prosthesis is fitted, e.g. the person with the knee replacement is standing upright with a straight leg. Extending downwardly and inwardly at an obtuse angle from the first flat section 17 is a second flat section 18, and this terminates at a third flat section 19 which in the arrangement described where the first flat section is vertical, would be horizontal and be engaged, in use, by the lowermost resected part of the patient's femur, which will normally be a flat surface interrupted by the intercondylar or patella groove.

Interconnecting the two condylar parts 13, 14, is a box-like bridging part 20 which is made up of a pair of vertical parallel spaced flat side walls 21, 22 respectively at the respective inner edges of the condylar parts adjacent the intercondylar groove. Bridging part 20 is provided with a flat top wall 23 which, in this embodiment, is parallel to the third flat sections 19 of the interior surface of the condylar parts. However the top wall 23 is formed with a central elongate slot 24 which is open at the open end of the intercondylar groove adjacent the respective free ends of the condylar parts. It will be noted that the wall 23 can either be complete, have a perforation/slot therein, or be absent.

The intercondylar groove extends into and centrally divides a fourth flat section 25 of the internal surface of the femoral flange 12, the flat section 25 extending outwardly and upwardly from the third flat section of each condylar part by an obtuse angle. The side walls 21, 22 substantially terminate at the upper part of this flat section 25 which extends into a fifth flat section 26 which extends upwardly from the section 25 and slightly inwardly therefrom. Part of the top wall 23 can terminate at this fifth flat section 26 as shown in FIG. 2, and the intercondylar groove terminates at the junction line 27 between the fourth and fifth sections. However this groove can terminate elsewhere, as required.

As described, the femoral component has its internal surface formed with a number of discrete flat sections with the junction lines between respective sections lying parallel to one another. This is the conventional shape of the interior surface of a femoral component, and is shown, for example, in British Patent Specification No. 2351236 and U.S. Pat. No. 6,413,279. With each of these prior art femoral components, the internal surface thereof is formed as five discrete flat sections with the first and fifth sections lying parallel to one another. With the femoral component 10 of FIG. 2, the first to third flat sections 17 to 19 are substantially shaped in the same way as with the prior art, with the third flat section 19 lying normal to the flat section 17. However instead of the remaining inner surface of the femoral flange containing two flat sections, it will be noted that with the femoral component 10 of FIG. 2, the remaining internal surface of the femoral flange 12 here comprises three separate flat sections, namely the fourth and fifth flat sections 25, 26 described above, and a sixth flat section 28 which extends to and defines the upper end of the femoral component. However instead of this sixth flat section 28 being parallel to the first flat section 17 as is the case with the terminal end section of the femoral flange of the prior art femoral components, this sixth section is here angled outwardly at, for example, 10°. Although the whole of the sixth flat section 28 is formed with this 'twisting' or 'divergence', it can be seen from FIG. 2 that this angle also effects the fifth flat section 26 to some degree, so that a junction line 29 between the sections 26 and 28 is not parallel to the junction line 27, but angles upwardly due to the 'twisting' described. As can be seen from FIG. 2, the sixth flat section 28 extends inwardly (in the upwards direction) at an angle from the fifth flat section 26, and that as a result of the 'twisting' described, the flat internal surface of the sixth flat section 28 is angled relative to a plane which is normal to the third flat section 19, the plane also being normal to the length of the intercondylar groove. Accordingly unlike with the prior art femoral components, the flat internal surface at the extremity of the femoral flange is not parallel to the first flat section 17 at the extremity of the condylar part 13, 14.

Figure 1:
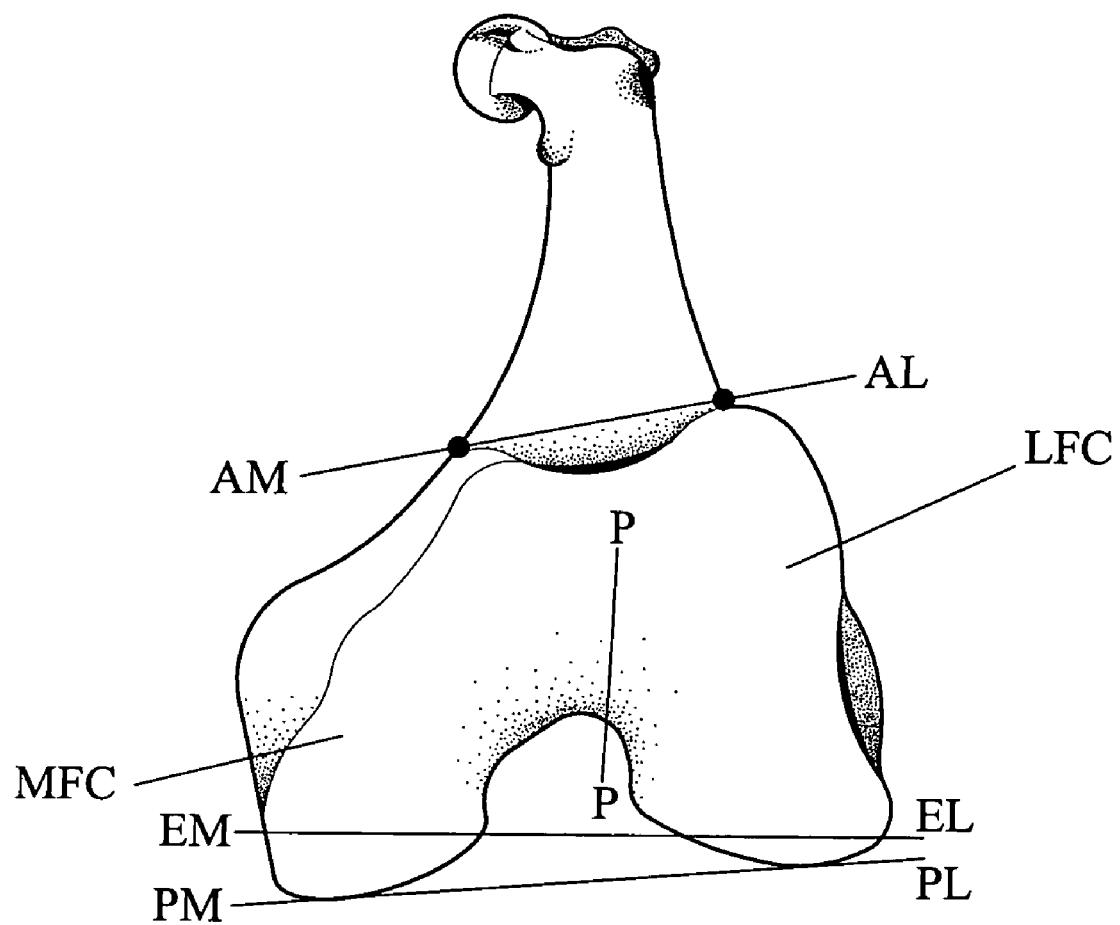
FIG. 1 is a perspective view of a femoral bone showing the femoral condyles and the femoral shaft.

With conventional femoral components, as hereinbefore described, the part of the femoral flange which extends inwards from the free extremity thereof has a flat inner surface which is parallel to the respective flat inner surfaces at the respective free extremities of the condylar parts. As described in relation to FIG. 1, the lower extremity of a femur is divided into two large eminences, namely the condyles, by an interval which presents a smooth depression in front called the trochlea, and a notch of considerable size behind, namely the intercondylar notch. The (external) lateral femoral condyle (LFC) is however, more prominent than the (internal) medial femoral condyle (MFC) anteriorally and is the broader both in the anterioposterior and transverse diameters. Two condyles directly continuous in front would form a smooth trochlea surface which articulates with the patella. In the introduction, in relation to FIG. 1, it has been described how, when resecting the distal end of the femur, a problem in fitting a conventional femoral component exists, with both options available to the surgeon being unsatisfactory. A femoral component of the invention overcomes/mitigates this problem.

The above described 'angling' or 'twisting' of the inner surface of the upper extremity of the femoral flange overcomes this problem in that it compensates for the difference in size between the outer and inner condyles at the lower extremity of the femur, thereby providing a much better securement and fit of the femoral component on the resected end of the femur.

A posterior cut on the femur parallel to either PM-PL or EM-EL is made according to surgeon preference, but because of the angled anterior cut then the surgeon can miss the lateral femoral flare at point AL and still make contact with the medial femoral anterior flare at point AM. As to the desirable angle for this anterior cut, it is thought that surface 17 and surface 28 should be at an angle of about 10° to each other, but this angle could be within a range of 3°-20°. The angle could be different with different sizes of component.

It will also be understood that the proportion of the interior surface of the femoral flange which is so 'twisted' can also be varied as required, particularly depending upon the nature and type of the resecting of the femur which is employed.

In an alternative embodiment, it is possible to provide the angled part of the femoral flange as part of a femoral component with the normal five surfaces, i.e. for use with the normal five cuts. Instead of angling surface 28, a compromise surface combining surfaces 26 and 28 is angled. The angled junction line 29 would replace the line 27 in such a configuration.

It is still however preferred to provide the six cuts, and thus to provide sixth surface 28 for the angled anterior cut from the viewpoint of surgical implantation. If the operation were to be performed with five conventional cuts, the cutting block would have to be used to cut the combined angled surface 26 and 28. Having cut an angled anterior surface there is then no scope for altering the medio-lateral position of the implant on the prepared femur.

Extending across the open end of the slot 24 in the bridging part 20 and being connected at its respective opposite ends to respective facing sides of the condylar parts 13 and 14 is a cam in the form of a cylindrical rod 30. This rod 30 extends normally from said parallel facing sides of the condylar parts, and it thus effectively lies parallel to the junction line 27.

Figure 4:
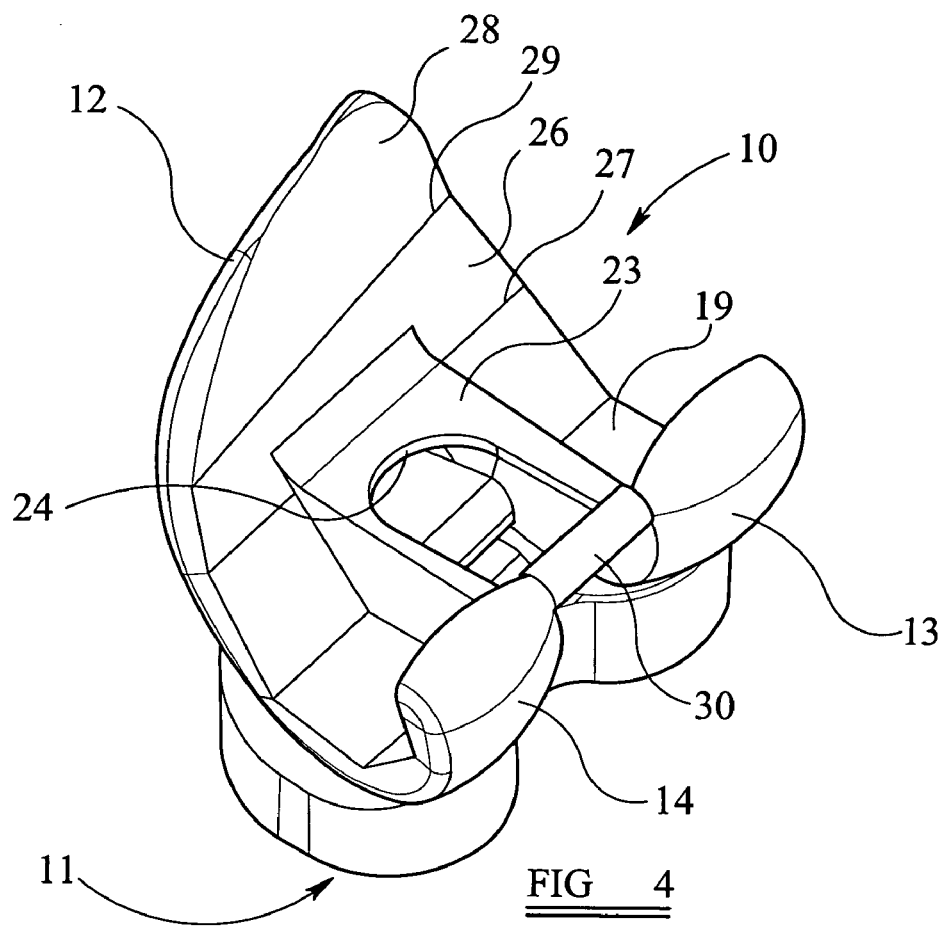
FIGS. 4 and 5 are respective perspective views in generally opposite directions of the components of FIGS. 1 and 2 assembled together, and shown at 0° flexion for a knee to which the prosthesis is fitted, in use.
Figure 5:
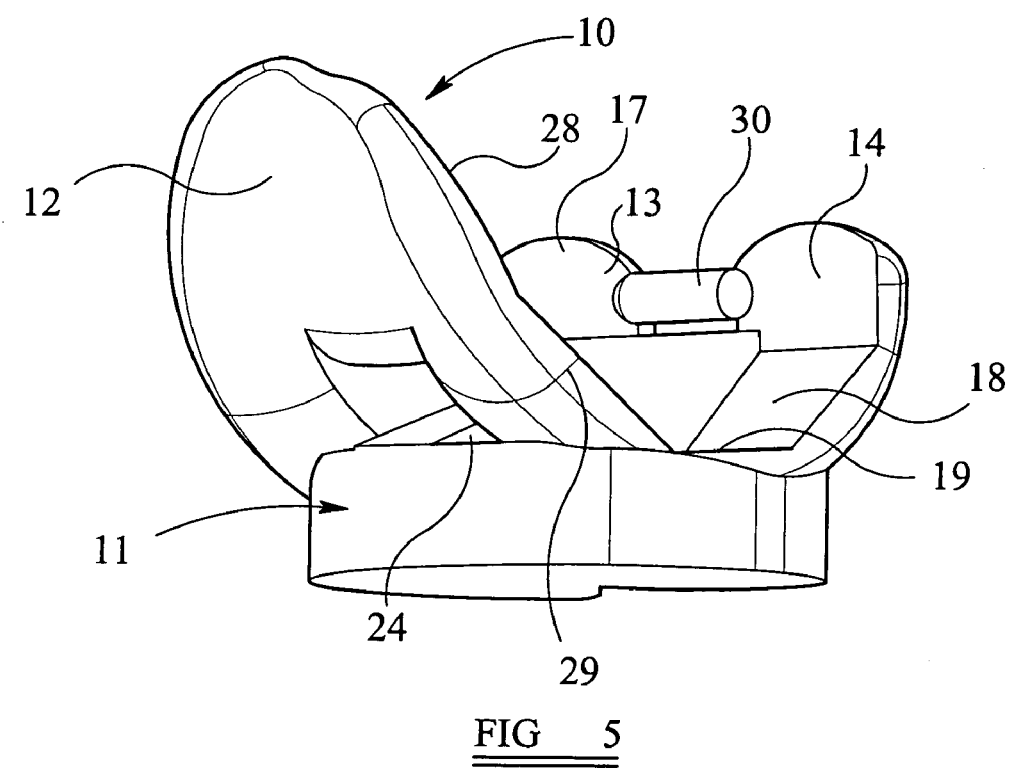
Figure 6:
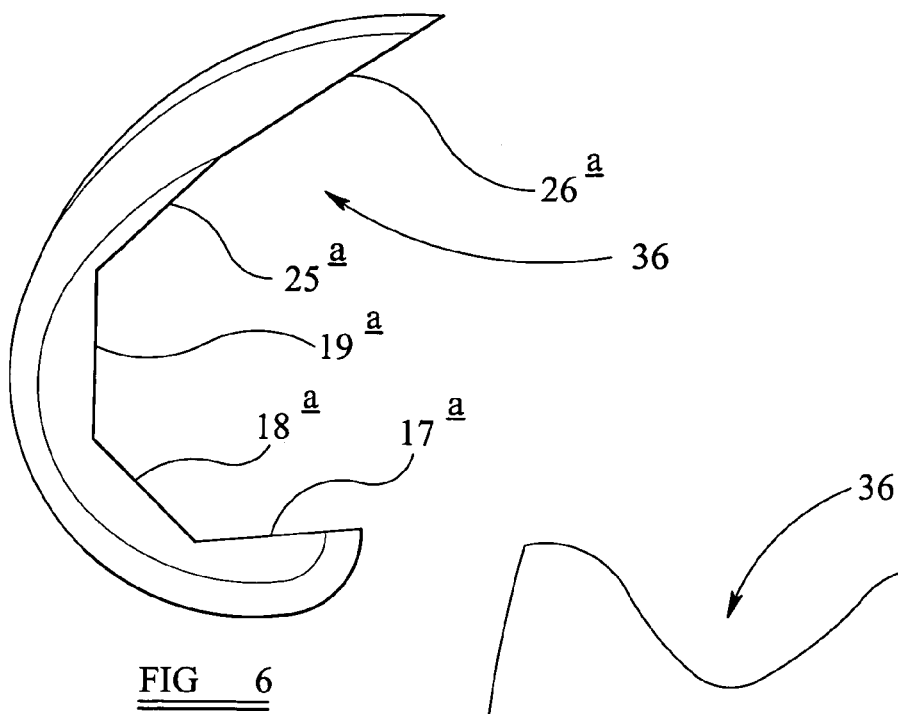
FIG. 6 is a side view of a trial femoral prosthesis component of a further aspect of the invention.

The meniscal or bearing component 11 is of generally known shape, being of similar shape, in plan view, to the tibial component, not shown, with which the bearing component is associated. The bearing component has a planar undersurface 31 which serves, in use, as an articulatory bearing surface engaged with the upper flat planar surface of the tibial component. The upper surface of the bearing component provides bearing surfaces 15, 16 described above to match the exterior surfaces of the condylar parts 13, 14 respectively. Centrally of the component 11, but towards the convex front peripheral side surface is formed a peg 32, with the opposite rear peripheral side surface of the bearing component being of dished or concave form, with the cam terminating short thereof. FIGS. 4 and 5 show the components 10 and 11 engaged together at 0° flexion for a knee to which the prosthesis is to be fitted.

As can be seen from FIG. 3, the peg has a body which rises with an upwardly angled flat top surface 33 from the front side surface to form an arcuate downwardly extending front nose part 34. Below this part 34 is a recess 35 which is of part-cylindrical concave form to match the cylindrical external surface of the rod 30 so that, as will be described, rod 30 can engage in the recess 35 and follow the shape of the recess thereby allowing the femoral component 10 to move relative to the bearing component 11 during flexion of the knee. In the example shown in FIG. 2, the recess 35 extends through approximately 180° from the surface of the bearing component 11 between the bearing surfaces 15, 16 to the lower edge of the front part 34. However the angle through which the recess extends can be varied as required, and the respective shapes of the inter-engaging parts of the rod and the peg can also be varied as required. This feature of the engagement forms the subject of my co-pending U.S. patent application titled "Knee Prosthesis", Ser. No. 11/351,529, filed concurrently herewith and incorporated herein by reference, to which reference should be made for further details.

FIGS. 6 to 10 show schematically a trial femoral prosthesis component 36 which has only five interior flat surfaces. These correspond to surfaces 17 to 19, 25 and 26 of the component of FIG. 2, and are numbered 17a to 19a, 25a and 26a respectively. It will also be noticed that, as compared to the component of FIG. 2, there is no box-like bridging part 20 on this trial component, merely a flat bridging part between the flat surfaces 17a.

In use, the component 36 can be applied to the femur and adjustment made for the precise medio-lateral position of the component on bone. Having decided on the position, the surgeon then cuts the angled anterior femur to match surface 28 through an angled slot in the trial implant. The trial implant is also used to cut the intercondylar region of the femur to accept the metallic box-like bridging part of the actual femoral component of the prosthesis.

Figure 7:
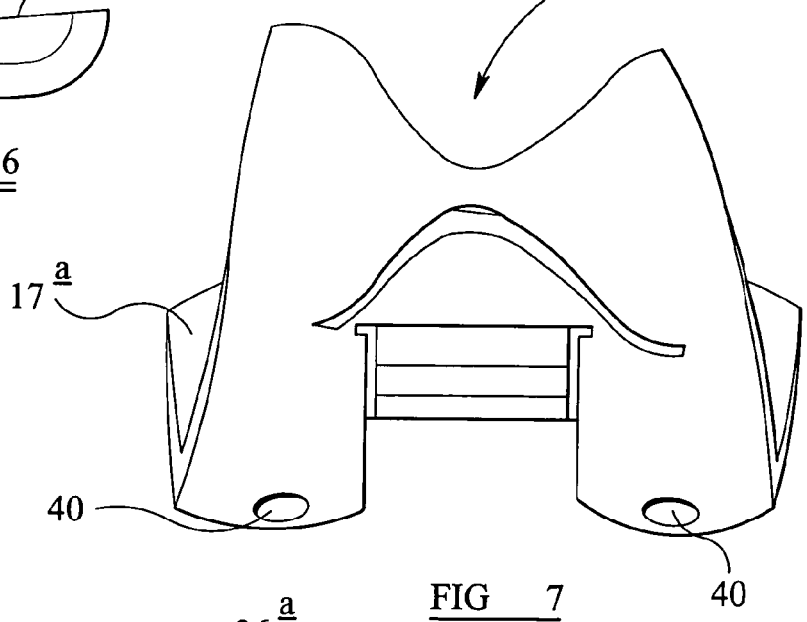
FIG. 7 is a front view of the component of FIG. 6.
Figure 8:
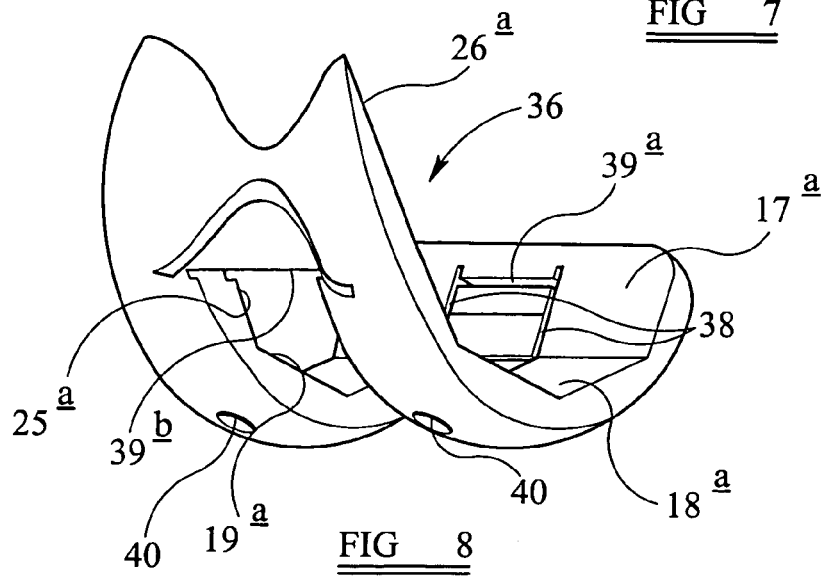
FIG. 8 is a front perspective view of the component of FIG. 6.
Figure 9:
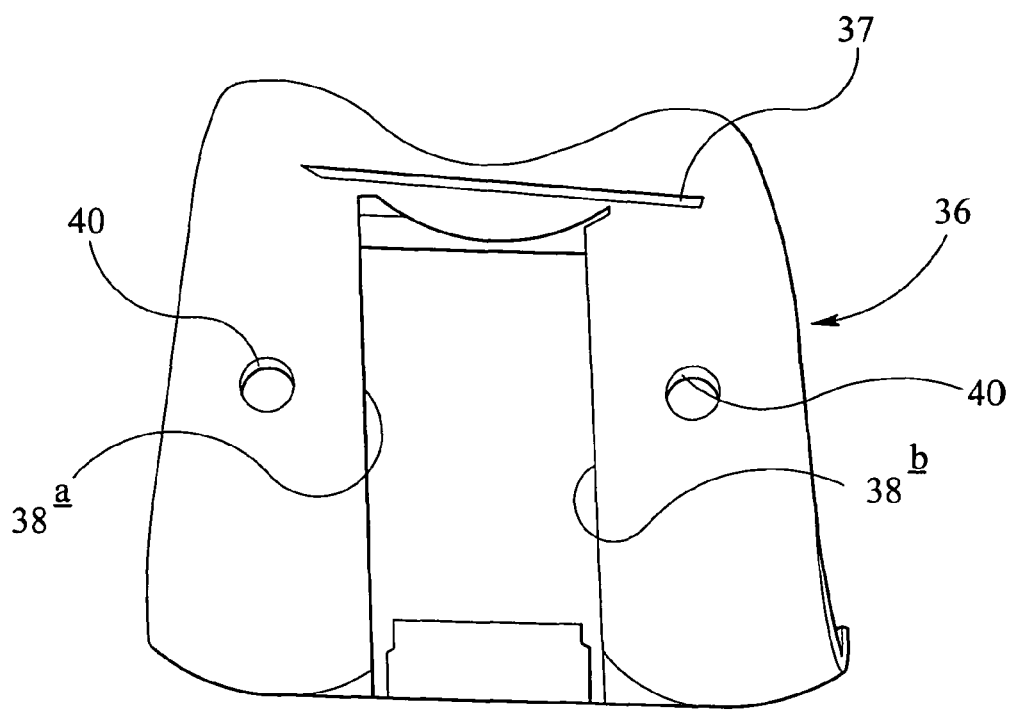
FIG. 9 is a view of part of the exterior surface of the trial component.
Figure 10:
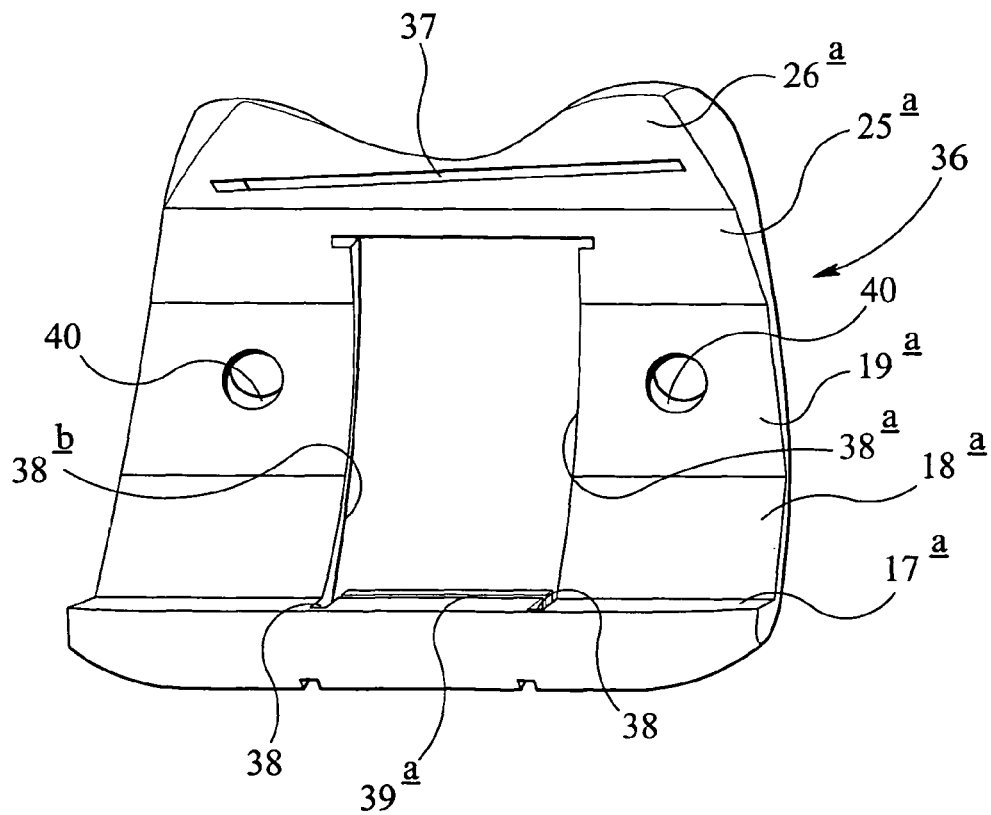
FIG. 10 is a view of the interior surface corresponding to the exterior surface of FIG. 9.

Accordingly the sixth cut is made through angled slot 37, the saw being inserted therethrough and producing the angle on the flat sixth cut. FIGS. 8 and 9 show a slot having lateral and medial sides 38a, 38b respectively to guide cuts for the sides of the flat bridging part, whilst FIGS. 7 and 8 show a slot 39a to guide the cut for the floor of the flat bridging part. FIGS. 7 and 8 also show a face 39b, along which a saw blade is inserted, in use, and directed through the bone into slot 39a to create the floor of the intercondylar box. Holes 40 are provided to drill for pegs (not shown) on the implant.

Although the inventive feature of this application can be used independently of the inventive feature of my co-pending U.S. patent application titled "Knee Prosthesis", Ser. No. 11/351,529, filed concurrently herewith, it is advantageous if they are used together, thereby producing a greatly improved congruent knee prosthesis.

The invention claimed is:

1. A knee prosthesis and a trial component therefore comprising:
a first femoral component, constituting the knee prosthesis, comprising a first femoral flange from which extend first lateral and medial condyles with a first intercondylar groove therebetween, the first condyles defining respective co-planar interior flat surfaces aligned at opposite sides of said first intercondylar groove to engage, in use, with respective flat lowermost surfaces of a resected femur, a part of the first femoral component extending to a free end of the first femoral component having a flat internal surface angled in a medio-lateral direction and relative to a plane which is normal to said flat surfaces and to the length of said first intercondylar groove; and
a second femoral component, constituting the trial component, comprising a second femoral flange from which extend second lateral and medial condyles with a second intercondylar groove therebetween, the second condyles defining respective co-planar interior flat surfaces aligned at opposite sides of said second intercondylar groove, the interior of the second femoral component being formed as five discrete flat sections such that the trial component can be applied to a resected femur and adjustment made for medio-lateral positioning of the trial component and the fifth section at a free end of the second femoral component having an angled slot therein to allow, in use, cutting of the anterior femur to form a flat cut which is angled in a medio-lateral direction and relative to a plane which is normal to said flat surfaces of the second condyles and to the length of the second intercondylar groove, to match said angled flat internal surface of the first femoral component, when the trial component is in a desired medio-lateral position since there will be no scope for altering the desired medio-lateral position once the angled flat cut is made.

2. A knee prosthesis and a trial component therefore as claimed in claim 1, wherein said part of the first femoral component is angled by a value in the range of approximately 3° to approximately 20° relative to said plane.

3. A knee prosthesis and a trial component therefore as claimed in claim 2, wherein said part of the first femoral component is angled by approximately 10° relative to said plane.

4. A knee prosthesis as claimed in claim 1, wherein an internal surface of the first femoral component extending away from said flat surfaces at opposite sides of the first intercondylar groove is formed as three flat sections at respective different angles relative to said plane.

5. A knee prosthesis and a trial component therefore as claimed in claim 1, wherein the interior of the first femoral component is formed as six discrete flat sections.

6. A knee prosthesis and a trial component therefore as claimed in claim 1, wherein the interior of the first femoral component is formed as five discrete flat sections.

7. A knee prosthesis and a trial component therefore as claimed in claim 1, comprising an open box-like bridging part interconnecting the first lateral and medial condyles.

8. A knee prosthesis and a trial component therefore as claimed in claim 1, wherein respective slots are formed at a flat bridging part between the second lateral and medial condyles to allow, in use cutting of the intercondylar region of the femur to accept a box-like bridging part of the first femoral component when fitted to the femur.

9. A knee prosthesis and a trial component therefore as claimed in claim 8, wherein two of the respective slots are formed as spaced, parallel continuations of the sides of the second intercondylar groove, a third slot being transverse thereto and spaced from the end of said second intercondylar groove at said flat bridging part.

10. A knee prosthesis and a trial component therefore as claimed in claim 1, comprising respective holes through said respective co-planar interior flat surfaces aligned at opposite sides of said second intercondylar groove.

11. A trial femoral component for a knee prosthesis, comprising a femoral flange from which extend lateral and medial condyles with an intercondylar groove therebetween, the condyles defining respective co-planar interior flat surfaces aligned at opposite sides of said intercondylar groove, the interior of the trial femoral component being formed as five discrete flat sections such that the trial femoral component can be applied to a resected femur and adjustment made for medio-lateral positioning of the trial femoral component and the fifth section at a free end of the trial femoral component having an angled slot therein to allow, in use, cutting of the anterior femur to form a flat cut which is angled in a medio-lateral direction and relative to a plane which is normal to said flat surfaces and to the length of the intercondylar groove, when the trial femoral component is in a desired medio-lateral position since there will be no scope for altering the desired medio-lateral position once the angled flat cut is made.

12. A trial femoral component as claimed in claim 11, wherein respective slots are formed at a flat bridging part between the lateral and medial condyles to allow, in use cutting of the intercondylar region of the femur to accept a box-like bridging part of an actual femoral component fitted to the femur.

13. A trial femoral component as claimed in claim 12, wherein two of the respective slots are formed as spaced, parallel continuations of the sides of the intercondylar groove, a third slot being transverse thereto and spaced from the end of said intercondylar groove at said flat bridging part.

14. A trial femoral component as claimed in claim 11, comprising respective holes through said respective co-planar interior flat surfaces aligned at opposite sides of said intercondylar groove.

15. A method of preparing a femur in preparation for the securing thereto of a first femoral component of a knee prosthesis, said first femoral component comprising a first femoral flange from which extend first lateral and medial condyles with a first intercondylar groove therebetween, the first condyles defining respective co-planar interior flat surfaces aligned at opposite sides of said first intercondylar groove to engage, in use, with respective flat lowermost surfaces of a resected femur, a part of the first femoral flange extending to a free end of the first femoral component having a flat internal surface angled in a medio-lateral direction and relative to a plane which is normal to said flat surfaces and to the length of said first intercondylar groove, the method comprising:

providing a second trial femoral component comprising a second femoral flange from which extend second lateral and medial condyles with a second intercondylar groove therebetween, the second condyles defining respective co-planar interior flat surfaces aligned at opposite sides of said second intercondylar groove, the interior of the second trial femoral component being formed as five discrete flat sections and the fifth section at a free end of the second trial femoral component having an angled slot therein, applying said second trial femoral component to the femur, adjusting the medio-lateral position of the second trial femoral component on the femur, and cutting the angled anterior femur through said slot to form a flat cut which is angled in a medio-lateral direction and relative to a plane which is normal to said flat surfaces of the second condyles and to the length of the second intercondylar groove to match an angled flat internal surface of said first femoral component, when the second trial femoral component is in a desired medio-lateral position since there will be no scope for altering the desired medio-lateral position once the angled flat cut is made.

16. A method as claimed in claim 15, including utilising respective slots at a flat bridging part of the second trial femoral component between the second lateral and medial condyles to cut the intercondylar region of the femur so that it can receive a box-like bridging part of said first femoral component interconnecting the first lateral and medial condyles thereof.

* * * * *